(12) United States Patent
Park

(10) Patent No.: US 12,708,371 B2
(45) Date of Patent: Aug. 18, 2026

(54) EMBOLIZATION DEVICE

(71) Applicant: SAMSUNG LIFE PUBLIC WELFARE FOUNDATION, Seoul (KR)

(72) Inventor: Hong Suk Park, Seoul (KR)

(73) Assignee: SAMSUNG LIFE PUBLIC WELFARE FOUNDATION, Seoul (KR)

( * ) Notice: Subject to any disclaimer, the term of this patent is extended or adjusted under 35 U.S.C. 154(b) by 397 days.

(21) Appl. No.: 17/773,534

(22) PCT Filed: Aug. 11, 2020

(86) PCT No.: PCT/KR2020/010598
§ 371 (c)(1),
(2) Date: Apr. 29, 2022

(87) PCT Pub. No.: WO2021/085815
PCT Pub. Date: May 6, 2021

(65) Prior Publication Data

US 2022/0378437 A1 Dec. 1, 2022

(30) Foreign Application Priority Data

Nov. 1, 2019 (KR) ........................ 10-2019-0138768

(51) Int. Cl.
*A61B 17/12* (2006.01)

(52) U.S. Cl.
CPC .. *A61B 17/12145* (2013.01); *A61B 17/12109* (2013.01)

(58) Field of Classification Search
CPC ........ A61B 17/12145; A61B 17/12109; A61B 17/12172; A61B 17/12177;
(Continued)

(56) References Cited

U.S. PATENT DOCUMENTS 6,123,715 A * 9/2000 Amplatz .................. A61F 2/90 606/151
6,152,144 A 11/2000 Lesh et al.
(Continued)

FOREIGN PATENT DOCUMENTS

JP 2001-286478 A 10/2001
JP 2003-529384 A 10/2003
(Continued)

OTHER PUBLICATIONS

International Search Report issued Nov. 13, 2020 in PCT/KR2020/010598 filed on Aug. 11, 2020, 3 pages.
(Continued)

*Primary Examiner* — Brooke Labranche
*Assistant Examiner* — Rachael L Geiger
(74) *Attorney, Agent, or Firm* — Oblon, McClelland, Maier & Neustadt, L.L.P.

(57) ABSTRACT

According to an embodiment, an embolic apparatus includes: a main body portion extending in a longitudinal direction; a plurality of first frame portions foldably connected to the main body portion; a plurality of second frame portions foldably connected to an end opposite to the other end of the main body portion connected to the plurality of first frame portions; and a blocking film portion connecting the plurality of first frame portions and covering the first frame portion, wherein the first frame portion and the second frame portion extend in directions away from each other.

4 Claims, 6 Drawing Sheets

(58) Field of Classification Search
CPC ........ A61B 17/12031; A61B 17/12045; A61B 2017/12127; A61B 17/12168; A61B 17/1204; A61F 6/146; A61F 6/22; A61F 6/225; A61F 6/24; A61F 2/01; A61F 2/0103; A61F 2002/016
See application file for complete search history.

(56) References Cited

U.S. PATENT DOCUMENTS 6,613,074 B1 9/2003 Mitelberg et al.
6,994,092 B2 2/2006 van der Burg et al.
10,426,590 B2 10/2019 Johnson et al.
10,660,645 B2 5/2020 Allen et al.
10,675,039 B2 6/2020 Allen et al.
11,229,440 B2 1/2022 Sqire et al.
2003/0057156 A1 3/2003 Peterson et al.
2004/0034366 A1 2/2004 van der Burg et al.
2012/0245619 A1* 9/2012 Guest .................... A61F 2/0105 606/200
2014/0276388 A1 9/2014 Allen et al.
2015/0005809 A1 1/2015 Ayres et al.
2015/0005810 A1* 1/2015 Center ............. A61B 17/12113 606/200
2016/0030047 A1 2/2016 Allen et al.
2016/0166257 A1 6/2016 Allen et al.
2017/0100112 A1 4/2017 van der Burg et al.
2017/0156840 A1* 6/2017 Edmiston ........... A61B 17/0057
2018/0206830 A1 7/2018 Khairkhahan et al.

FOREIGN PATENT DOCUMENTS

JP 2005-508201 A 3/2005
JP 2016-509922 A 4/2016
JP 2016-513544 A 5/2016
JP 2018-506391 A 3/2018
KR 10-2015-0127135 A 11/2015
KR 10-2017-0056653 A 5/2017
WO WO 00/27292 A1 5/2000
WO WO 02/071977 A2 9/2002
WO WO 2014/140325 A1 9/2014
WO WO 2014/152365 A2 9/2014
WO WO 2016/041961 A2 3/2016

OTHER PUBLICATIONS

Korean Notice of Reason for Refusal, issued Dec. 21, 2021 in Korean Application No. 10-2019-0138768 filed on Nov. 1, 2019, 11 pages (with English Translation).
European Search Report issued Sep. 28, 2023 in EU 20882473.0 (filed Aug. 11, 2020), 8 pages.

* cited by examiner

EMBOLIZATION DEVICE

TECHNICAL FIELD

The present disclosure relates to an embolic apparatus, more particularly, to an embolic apparatus that is easy to be installed and capable of immediately blocking blood flow.

BACKGROUND ART

Generally, an embolic apparatus is inserted in a blood vessel to block bleeding during interventional procedures, diseases, such as arteriovenous fistula, or various types of blood flow.

As an example of the embolic apparatus in the related art, a coil-shaped embolic apparatus has been used. However, it has been difficult to accurately insert the coil-shaped apparatus in a desired portion inside an object, such as a blood vessel, coil-shaped embolic apparatus is moved after insertion, the coil has to be wound several times to have an embolic effect, and the process of inserting the coil-shaped embolic apparatus inside the object is technically difficult and a skilled user has to use the coil-shaped embolic apparatus.

In addition, although insertion of an amplatzer vascular plug (AVP), which is for compensating for the shortcomings of the coil-shaped embolic apparatus, is relatively stable, a thick conduit or guide tube is required. Also, it is difficult to insert the AVP in blood vessels with severe curvature or relatively thin vessels, if the AVP is inserted forcibly, the blood vessels may be damaged, and due to structural limits, an immediate occlusion has not been possible or there has been risks of reopening.

The related art of the present disclosure is disclosed in KR patent application no. 10-2015-0127135 (published on Nov. 16, 2015 and titled "EMBOLIZATION SYSTEM)".

DESCRIPTION OF EMBODIMENTS

Technical Problem

The present disclosure provides an embolic apparatus that is easy to install due to including a foldable first frame portion and a foldable second frame portion and a blocking film portion covering the first frame portion and that may immediately block blood flow.

However, these problems are examples, and the scope of the present disclosure is not limited thereby.

Solution to Problem

In accordance with an aspect of the disclosure, an embolic apparatus may include: a main body portion extending in a longitudinal direction; a plurality of first frame portions foldably connected to the main body portion; a plurality of second frame portions foldably connected to an end opposite to the other end of the main body portion connected to the plurality of first frame portions; and a blocking film portion connecting the plurality of first frame portions and covering the first frame portion, wherein the first frame portion and the second frame portion may extend in directions away from each other.

According to an embodiment of the disclosure, the embolic apparatus may further include a bent portion on an end opposite to the other end of the second frame portion connected to the main body portion.

According to an embodiment of the disclosure, the second frame portion may include: a fixing frame having the bent portion thereon; and a contact frame intersecting with a side of the fixing frame having the bent portion thereon and being in contact with an inner circumferential surface of an object.

According to an embodiment of the disclosure, the fixing frame and the contact frame may be welding coupled at a region in which the fixing frame intersects with the contact frame.

In accordance with another aspect of the disclosure, an embolic apparatus may include: a main body portion extending in a longitudinal direction; a plurality of first frame portions foldably connected to the main body portion; a plurality of second frame portions arranged to face the plurality of first frame portions, extending in a direction away from the plurality of first frame portions, and foldably connected to the main body portion; and a blocking film portion provided in plural and provided to each independently cover the plurality of first frame portions and the plurality of second frame portions.

According to an embodiment of the disclosure, the embolic apparatus may further include a bent portion on an end opposite to the other end of the second frame portion connected to the main body portion.

Other aspects, features, and advantages other than those described above will become apparent from the following drawings, claims, and detailed description.

Advantageous Effects of Disclosure

An embolic apparatus according to an embodiment may be easily moved inside an object, such as a blood vessel, by including a first frame portion and a second frame portion that are formed to extend in directions away from each other and are foldably connected to a main body portion, and may be stably positioned to be fixed inside the object as the second frame portion is unfolded.

In addition, because the blocking film portion covers the first frame portion, blood flow may be blocked in both sides of the blocking film portion.

In addition, a fixing frame may be prevented from being embedded in the object beyond a predetermined depth due to the contact frame, and damage to the object due to excessive insertion may be prevented.

The scope of the invention is not limited by the above effects.

BEST MODE

Figure 1:
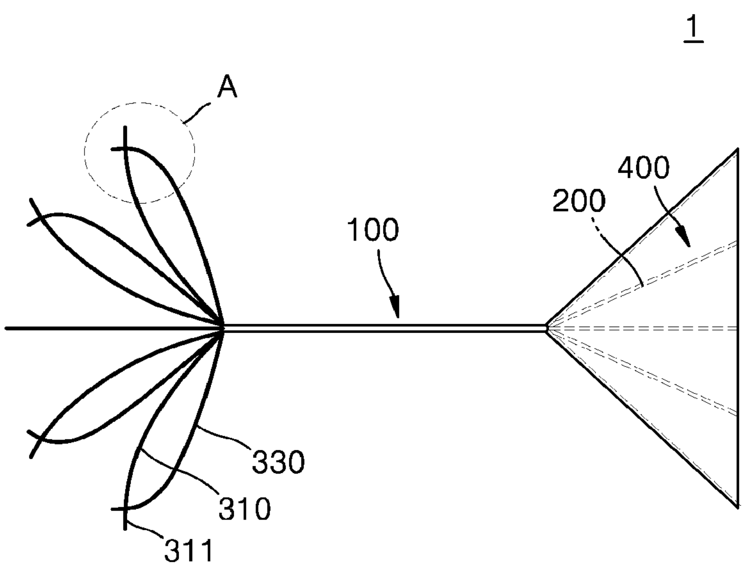
FIG. 1 shows a side view of an embolic apparatus according to an embodiment.

Since the present disclosure may be applied in various ways and have various embodiments, certain embodiments will be illustrated in the drawings and described in detail in the detailed description. Effects, features, and a method of achieving the inventive concept will be obvious by referring to example embodiments of the inventive concept with reference to the attached drawings. The inventive concept may, however, be embodied in many different forms and should not be construed as being limited to the embodiments set forth herein.

Hereinafter, embodiments of the present disclosure will be described in detail with reference to the accompanying drawings, and when describing with reference to the drawings, the same or corresponding components are assigned the same reference numerals, and redundant descriptions thereof will be omitted.

In the following examples, the terms "first" and "second" are used for the purpose of distinguishing one component from other components and not for limiting the meaning.

In the below embodiments, the terms of a singular form may include plural forms unless otherwise mentioned.

It will be further understood that the terms "comprises" and/or "comprising" used herein specify the presence of stated features or elements, but do not preclude the presence or addition of one or more other features or elements.

In the below embodiments, when a part such as a film, region, element is above or on another part, this includes not only the case in which the part is directly above the other part, but also the case in which another film, region, element, and the like are intervened in the middle.

In the drawings, the sizes of elements may be exaggerated for clarity of illustration. For example, the size and thickness of each element shown in the drawings are arbitrarily shown for convenience of description, and thus the present disclosure is not necessarily limited to what is shown.

In the case where an embodiment may be implemented differently, a specific process order may be performed differently from the described order. For example, two processes described in succession may be practically performed simultaneously, or in an opposite order to which they are described.

In the following embodiments, when films, regions, elements are connected, this includes not only the case in which the films, regions, and elements are directly connected, but also the case in which another film, region, element, and the like are intervened in the middle, thereby indirectly connecting the films, regions, elements, and the like.

Figure 2:
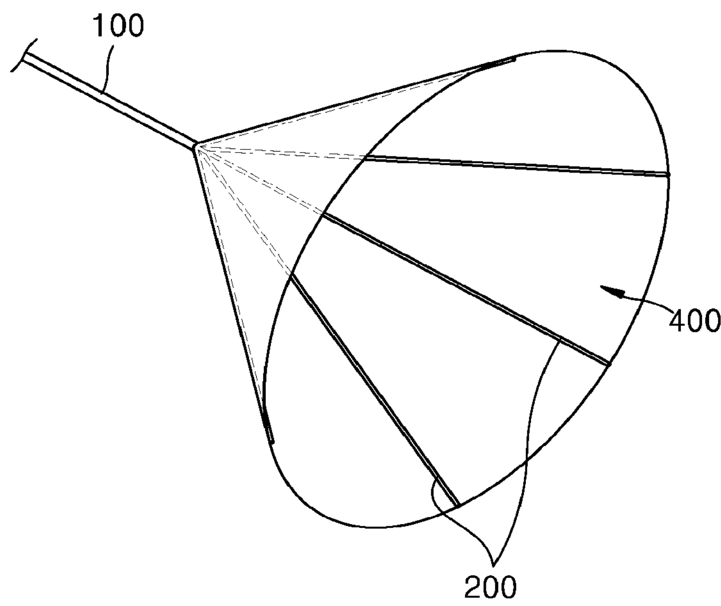
FIG. 2 shows a partial perspective view of a first frame portion and a blocking film portion according to an embodiment.
Figure 3:
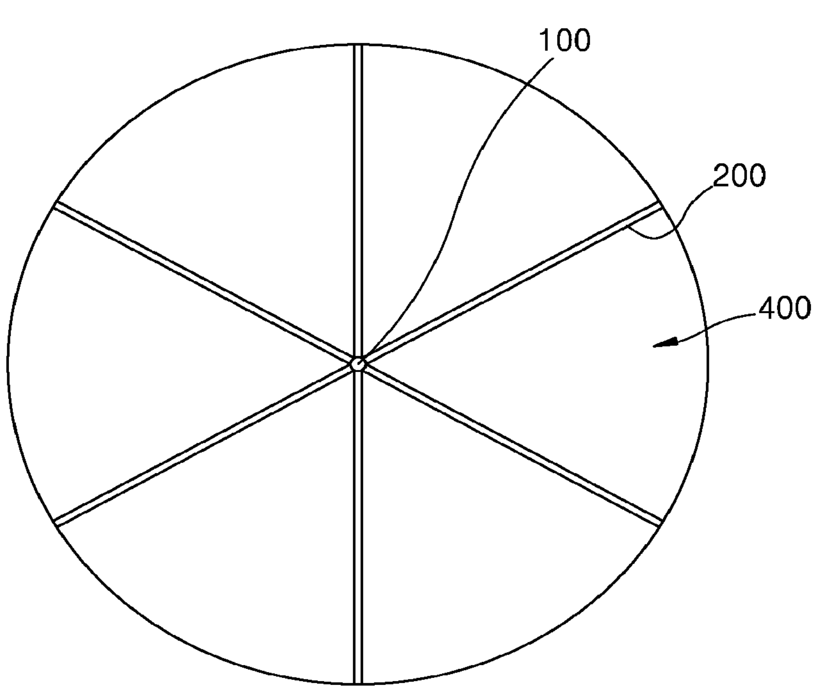
FIG. 3 shows a front view of the first frame portion and the blocking film portion according to an embodiment.
Figure 4:
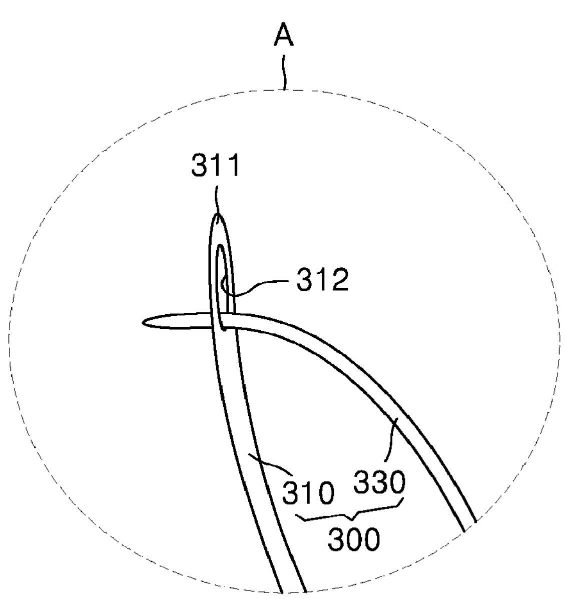
FIG. 4 shows an enlarged drawing of the A part in FIG. 1.
Figure 5:
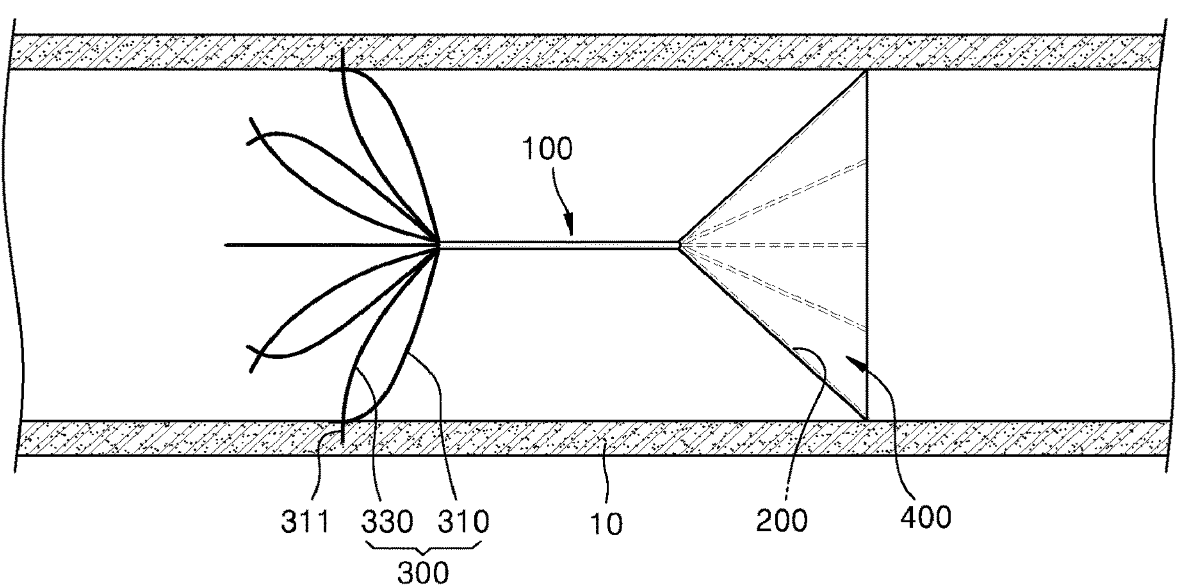
FIG. 5 shows an embolic apparatus according to an embodiment of the present disclosure arranged inside an object.

FIG. 1 shows a side view of an embolic apparatus according to an embodiment. FIG. 2 shows a partial perspective view of a first frame portion and a blocking film portion according to an embodiment. FIG. 3 shows a front view of the first frame portion and the blocking film portion according to an embodiment. FIG. 4 shows an enlarged diagram of part A in FIG. 1. FIG. 5 shows an embolic apparatus according to an embodiment of the present disclosure arranged inside an object.

Referring to FIGS. 1 to 6, an embolic apparatus 1 according to an embodiment of the present disclosure may include a main body portion 100, a first frame portion 200, a second frame portion 300, and a blocking film portion 400.

The embolic apparatus 1 according to an embodiment of the present disclosure may be arranged inside an object 10, such as a blood vessel, and may block bleeding during interventional procedures, diseases, such as arteriovenous fistulas, or various types of blood flow.

Referring to FIGS. 1 to 3 and 5, the main body portion 100 according to an embodiment of the present disclosure may be formed to extend in a longitudinal direction. The main body portion 100 may be arranged inside the object 10, such as a blood vessel, and the first frame portion 200 and the second frame portion 300, as described below, may be foldably connected to both ends of the main body portion 100.

Referring to FIGS. 1 to 3 and 5, the first frame portion 200 according to an embodiment of the present disclosure may be foldably connected to an end (the right side according to FIG. 1) of the main body portion 100. A plurality of two or more first frame portions 200 may be provided, and the plurality of first frame portions 200 may be connected to the main body portion 100.

Referring to FIGS. 1 to 3, the first frame portion 200 according to an embodiment of the present disclosure may be unfolded to form a certain angle with the main body portion 100, and in an unfolded state, the first frame portion 200 may be parallel to a longitudinal direction of the main body portion 100 and may move in the object 10, such as a blood vessel.

Referring to FIG. 3, according to an embodiment of the present disclosure, an end of the plurality of first frame portions 200, to which the main body portion 100 is connected, may be fixed, and the other end opposite to the end may spread out radially from the end (the right end according to FIG. 1) of the main body portion 100 connected to the first frame portion 200.

Five first frame portions 200 are provided in the present disclosure, but embodiments are not limited thereto. Therefore, embodiments may be modified, such as less than five or more than six first frame portions.

Referring to FIGS. 1 to 5, the plurality of first frame portions 200 according to an embodiment of the present disclosure may be coupled to the blocking film portion 400 to be described below. In particular, the blocking film portion 400 may connect between different first frame portions 200 and may be folded or unfolded.

The blocking film portion 400 may connect between the different first frame portions 200 and may block the flow of fluids, such as blood flow between the plurality of first frame portions 200. The blocking film portion 400 may be formed of a film of polytetrafluoroethylene (PTFE) and dacron material.

Referring to FIGS. 1, 4, and 5, the second frame portion 300 according to an embodiment may be connected to an end (the left side according to FIG. 1) opposite to the other end (the right side according to FIG. 1) of the main body portion 100 connected to the first frame portion 200 and the second frame portion 300 may be provided in plural.

Referring to FIGS. 1 and 5, the second frame portion 300 according to an embodiment may be formed to extend in a direction away from the first frame portion 200.

Particularly, the first frame portion 200 may be connected to the right end (according to FIG. 1) of the main body portion 100 and may be unfolded in an outward direction (right direction according to FIG. 1), and the second frame portion 300 may be connected to the left end (according to FIG. 1) of the main body portion 100 and may be unfolded in an outward direction.

In other words, the first frame portion 200 may be unfolded to form an obtuse angle with the main body portion 100 in the outward direction (the right side according to FIG. 1), and the second frame portion 300 may be unfolded to form an obtuse angle with the main body portion 100 in the outward direction (the left side according to FIG. 1).

Referring to FIGS. 1, 4, and 5, the second frame portion 300 according to an embodiment may include a fixing frame 310 and a contact frame 330.

Referring to FIGS. 1, 4, and 5, the fixing frame 310, which is connected to the main body portion 100, may have a bent portion 311 formed on an end (the left end according to FIG. 1) opposite to the other end connected to the main body portion 100.

Referring to FIGS. 1, 4, and 5, the bent portion 311 may be formed in an outward direction at a certain angle to a longitudinal direction of the second frame portion 300. The bent portion 311 may be formed in a curved shape having a certain radius of curvature.

Because the bent portion 311 is formed, the bent portion 311 may be inserted at a certain depth into the object 10, such as a blood vessel, and thus, the embolic apparatus 1 including the main body portion 100, the first frame portion 200, the second frame portion 300, and the blocking film portion 400 may be fixed and may block the flow of fluids, such as blood.

Referring to FIGS. 1 and 4, a hole portion 312 may be formed in the fixing frame 310 according to an embodiment.

The hole portion 312 may be formed to extend in a longitudinal direction of the fixing frame 310, and the contact frame 330 to be described below may pass through the hole portion 312 and be coupled to the fixing frame 310.

Because the hole portion 312 is formed in the fixing frame 310 to extend in the longitudinal direction of the fixing frame 310, the contact frame 330 may pass through the hole portion 312 and be coupled to the fixing frame 310, and when the contact frame 330 is in contact with an inner circumferential surface of the object 10, the fixing frame 310 may be prevented from being inserted more into the object 10.

Referring to FIGS. 1 and 4, the fixing frames 310 according to an embodiment may be formed concavely in an outward direction from the main body portion 100. Therefore, an end of the fixing frame 310 having the bent portion 311 formed thereon may face an upward and downward direction (according to FIG. 1) and may be inserted into the object 10, such as a blood vessel wall.

Referring to FIGS. 1 and 4, the fixing frame 310 and the contact frame 330 according to an embodiment may have radii of curvature in different directions and be coupled to each other in a second point.

In particular, the fixing frame 310 and the contact frame 330 may be coupled to each other at a first point, which is an end of the main body portion 100 (a left end according to FIG. 1).

According to an embodiment, the fixing frame 310 may be formed concavely in an outward direction from the main body portion 100, and the contact frame 330 may be formed convexly in an outward direction from the main body portion 100.

Therefore, the contact frame 330 may pass through the hole portion 312 formed in a longitudinal direction in the fixing frame 310, and may be coupled to the fixing frame 310 at the second point of the fixing frame 310, in which the hole portion 312 is formed.

Referring to FIGS. 1, 4, and 5, the contact frame 330 according to an embodiment, which intersects with one side of the fixing frame 310 having the bent portion 311 formed thereon, may be in contact with an inner circumferential surface of the object 10.

Referring to FIGS. 1 and 4, the contact frame 330 according to an embodiment may pass through the fixing frame 310 and be welding-coupled to the fixing frame 310. The contact frame 330 may pass through the hole portion 312 formed in the fixing frame 310 and intersect with the fixing frame 310.

However, embodiments are not limited thereto, and various modified embodiments, such as a pin fixing method, knot fixing method, etc., in regions where the fixing frame 310 intersects with the contact frame 330, may be possible.

In the present disclosure, the hole portion 312 may be formed in the fixing frame 310, the contact frame 330 may pass through the hole portion 312 formed in the fixing frame 310 and be in contact with the inner circumferential surface of the object 10, but embodiments are not limited thereto, and various modified embodiments, such as a hole portion being formed in the contact frame 330, and the fixing frame 310 passing through the hole portion formed in the contact frame 330 to be inserted into the object 10, may be possible.

In this case, the fixing frame 310 may be coupled to and positioned to be fixed in the hole portion formed in the contact frame 330, and only a predetermined length of the fixing frame 310 that passed through the hole portion formed in the contact frame 300 may be inserted into the object 10.

Referring to FIG. 4, the hole portion 312 may be formed in the fixing frame 310 in a longitudinal direction to be as long as a predetermined length.

Because the contact frame 330 passes through the hole portion 312 and comes into contact with the inner circumferential surface of the object 10, the fixing frame 310, particularly, the bent portion 311, may be prevented from being embedded in the object 10, such as a blood vessel, more than the predetermined depth and thus damaging the blood vessel.

In other words, there are cases in which, when the blood flow is fast or the blood pressure is high when the fixing frame 310 is embedded in the object 10, pressure is continuously transferred to the first frame portion 200 and the blocking film portion 400, thus causing the fixing frame 310 to be inserted into the object 10 more than necessary and thus damaging the blood vessel. Such a phenomenon may be prevented.

Referring to FIGS. 1 and 4, the contact frame 330 according to an embodiment may be formed convexly in an outward direction from the main body portion 100, different from the fixing frame 310 formed concavely in an outward direction from the main body portion 100.

Because the contact frame 330 is formed convexly in an outward direction from the main body portion 100, an end of the contact frame 330 may be positioned to be in gentle contact with the inner circumferential surface of the object 10, not in a direction that may pierce the object 10, such as a blood vessel.

In addition, because the contact frame 330 passes through the hole portion 312 formed in the fixing frame 310, the contact frame 330 may be in contact with the inner circumferential surface of the object 10 as much as a predetermined length, and the fixing frame 310 may be prevented from being inserted into the object 10 more than a predetermined depth.

Referring to FIGS. 1 to 3 and 5, the blocking film portion 400 according to an embodiment, which connects the plurality of first frame portions 200, may cover the first frame portion 200.

Particularly, the blocking film portion 400 may connect between the first frame portions 200 that are different from each other, may be folded or unfolded, may move inside the object 10, such as a blood vessel, when the first frame portion 200 is folded, and when the first frame portion 200 is unfolded in a predetermined position, the blocking film portion 400 may also be unfolded.

The blocking film portion 400 according to an embodiment may connect between different first frame portions 200 and may block the flow of fluids, such as blood flow, between the plurality of first frame portions 200.

The blocking film portion 400 according to an embodiment may be formed of a film of materials such as, polytetrafluoroethylene (PTFE), dacron, and the like.

The principle of operation and effect of the embolic apparatus 1 will be described.

Referring to FIGS. 1 to 5, an embolic apparatus 1 according to an embodiment may include a main body portion 100, a first frame portion 200, a second frame portion 300, and a blocking film portion 400. The first frame portion 200 and the second frame portion 300 may be coupled to both ends of the main body portion 100, and the first frame portion 200 and the second frame portion 300 may be formed to extend in directions away from each other.

Particularly, the first frame portion 200 may be unfolded in the right direction from the right end (according to FIG. 1) of the main body portion 100, and the second frame portion 300 may be unfolded in the left direction from the left end (according to FIG. 1) of the main body portion 100.

In the embolic apparatus 1 according to an embodiment, the first frame portion 200 and the second frame portion 300 may be arranged in a predetermined position inside the object 10 in a folded state inside a conduit having a hollow interior (not shown).

When the conduit accommodating the embolic apparatus 1 is arranged in a predetermined position inside the object 10, the embolic apparatus 1 may exit from the conduit, the first frame portion 200 and the second frame portion 300 may be unfolded in an outward direction with respect to the main body portion 100, and the position of the embolic apparatus 1 may be fixed.

Referring to FIGS. 1 and 5, the first frame portion 200 may be provided in plural, and the plurality of first frame portions 200 may be coupled to each other at an end (the right end according to FIG. 1) of the main body portion 100. The plurality of first frame portions 200 may be coupled to the blocking film portion 400.

Referring to FIGS. 1 to 3 and 5, the blocking film portion 400 according to an embodiment may be coupled to the plurality of first frame portions 200 and may connect between the plurality of first frame portions 200.

Referring to FIG. 5, when the embolic apparatus 1 moves inside the object 10, such as a blood vessel, the first frame portion 200 may be in a folded state and then be unfolded at a predetermined position, the blocking film portion 400 coupled to the first frame portion 200 is unfolded, and the flow of fluids, such as blood, in the object 10 may be blocked.

Referring to FIGS. 1 and 4, the second frame portion 300 may be coupled to the other end (the left end according to FIG. 1) opposite to the end (the right end according to FIG. 1) of the main body portion 100 to which the first frame portion 200 according to an embodiment is coupled.

The second frame portion 300 may be provided in plural, and each of the second frame portions 300 may include the fixing frame 310 and the contact frame 330.

The bent portion 311 may be formed on the other end of the fixing frame 310 opposite to the end connected to the main body portion 100, and may be inserted in an inner wall of the object 10. The contact frame 330, which may be coupled to the fixing frame 310, may pass through the hole portion 312 formed in the fixing frame 310 and be coupled to the fixing frame 310.

The hole portion 312 may be formed to extend in a predetermined length on the fixing frame 310, and the contact frame 330 may pass through the hole portion 312 to be coupled to the fixing frame 310 at a second point by welding etc.

The fixing frame 310 and the contact frame 330 may have radii of curvature in different directions and particularly, the fixing frame 310 may be concavely formed in an outward direction from the main body portion 100, and the contact frame 330 may be convexly formed in an outward direction from the main body portion 100.

Because the contact frame 330 is convexly formed in an outward direction from the main body portion 100, an end of the contact frame 330 may be arranged in parallel to and in stable contact with the inner circumferential surface of the object 10.

In addition, because the contact frame 330 passes through the hole portion 312 formed in the fixing frame 310, the fixing frame 310 including the hole portion 312 may be prevented from being embedded in the object 10 more than a predetermined depth.

In addition, damage to the object 10 due to pressure caused by blood flow inside the object 10 when the fixing frame 310 is embedded in the object 10 may be prevented.

Figure 6:
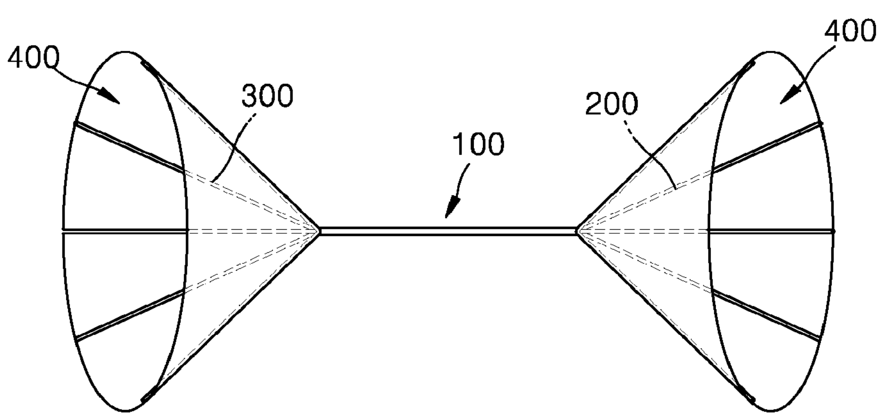
FIG. 6 shows a perspective view of an embolic apparatus according to another embodiment.

Hereinafter, the structure, principle of operation, and effect of an embolic apparatus according to another embodiment are described. FIG. 6 shows a perspective view of an embolic apparatus according to another embodiment.

An embolic apparatus 2 according to an embodiment may include a main body portion 100, a first frame portion 200, a second frame portion 300, and a blocking film portion 400.

Referring to FIG. 6, the blocking film portion 400 according to an embodiment may be provided in plural, and the plurality of blocking film portions 400 may each independently cover the first frame portion 200 and the second frame portion 300.

Therefore, the plurality of blocking film portions 400 may be arranged in both sides (the left and right sides according to FIG. 6) of the main body portion 100, and may effectively block flow, such as blood flow, inside the object 10.

Although the shape of the second frame portion 300 arranged on the left side (according to FIG. 6) of the main body portion 100 is illustrated to be the same as that of the first frame portion 200, embodiments are not limited thereto, and various modified embodiments of the second frame portion 300 according to an embodiment, particularly, a structure including the fixing frame 310 and the contact frame 330, may be possible.

When the second frame portion 300 according to another embodiment is formed to be the same as the second frame portion 300 according to an embodiment, the blocking film portion 400 may cover the second frame portion 300 only to a region where the fixing frame 310 intersects with and is coupled to the contact frame 330.

Because the structures of the main body portion 100, the first frame portion 200, and the second frame portion 300 of the embolic apparatus 2 according to another embodiment are the same as those of the embolic apparatus 1 according to an embodiment except the blocking film portion 400 provided in plural may each independently cover the first frame portion 200 and the second frame portion 300, detailed descriptions regarding the same structures are omitted.

The specific implementations described herein are illustrative examples of embodiments and are not intended to otherwise limit the scope of embodiments in any way. For the sake of brevity, conventional electronics, control systems, software development and other functional aspects of the systems may not be described in detail. Furthermore, the connecting lines, or connectors shown in the various figures presented are intended to represent exemplified functional relationships and/or physical or logical connections between the various elements. Many alternative or additional functional relationships, physical connections, or logical connections may be present in a practical device. Moreover, no item or component is essential to the practice of embodiments unless the element is specifically described as "essential" or "critical."

Therefore, the spirit of the present disclosure is not limited to the embodiments described above, and not only the scope of the claims below but also the scope equivalent to or changed from the claims will belong to the scope of the spirit of the present disclosure.

INDUSTRIAL APPLICABILITY

Provided is an embolic apparatus according to embodiments of the present disclosure. In addition, the embodiments of the present disclosure may be applied to an embolic apparatus inserted into a blood vessel and used industrially, for blocking bleeding during interventional procedures, diseases, such as arteriovenous fistulas, or various types of blood flow.

The invention claimed is:

1. An embolic apparatus comprising: a main body portion extending in a longitudinal direction; a plurality of first frame portions foldably connected to the main body portion; a plurality of second frame portions foldably connected to an end opposite to the other end of the main body portion connected to the plurality of first frame portions; and a blocking film portion connecting the plurality of first frame portions and covering the plurality of first frame portions; wherein the plurality of first frame portions and the plurality of second frame portions extend in directions away from each other, wherein each of the plurality of second frame portions comprises: a fixing frame having a bent portion thereon; and a contact frame extending through and intersecting with the fixing frame; and a hole portion formed in the fixing frame to extend longitudinally; wherein the hole portion is formed only in the fixing frame and the contact frame is free of a hole portion at a location intersecting the fixing frame, wherein the contact frame passes completely through the hole portion in a single direction and is coupled to the fixing frame, wherein the fixing frame is formed to be concave in an outward direction from the main body portion, and the contact frame is formed to be convex in the outward direction from the main body portion, wherein a maximum radial distance of the contact frame from the main body portion is greater than a radial distance of the bent portion from the main body portion, wherein the contact frame extends beyond the fixing frame and is positioned to contact an inner circumferential surface of a target object prior to the bent portion reaching a predetermined penetration depth, thereby mechanically limiting penetration depth of the bent portion by providing a physical stop that prevents the bent portion from being embedded in the target object beyond the predetermined depth.

2. The embolic apparatus of claim 1, wherein the fixing frame and the contact frame are weldably coupled at a region in which the fixing frame intersects with the contact frame.

3. An embolic apparatus comprising: a main body portion extending in a longitudinal direction; a plurality of first frame portions foldably connected to the main body portion; a plurality of second frame portions arranged to face the plurality of first frame portions, extending in a direction away from the plurality of first frame portions, and foldably connected to the main body portion; a blocking film portion provided in plural to each independently cover the plurality of first frame portions and the plurality of second frame portions; and a bent portion on a distal end of one of the plurality of second frame portions, wherein the distal end is opposite to a proximal end of the second frame portion connected to the main body portion; wherein the one of the plurality of second frame portions comprises: a fixing frame having the bent portion thereon; a contact frame extending through and intersecting with the fixing frame; and a hole portion formed in the fixing frame to extend longitudinally, wherein the hole portion is formed only in the fixing frame and the contact frame is free of a hole portion at a location intersecting the fixing frame, wherein the contact frame passes completely through the hole portion in a single direction and is coupled to the fixing frame, wherein the fixing frame is formed to be concave in an outward direction from the main body portion, and the contact frame is formed to be convex in the outward direction from the main body portion, wherein a maximum radial distance of the contact frame from the main body portion is greater than a radial distance of the bent portion from the main body portion, wherein the contact frame extends beyond the fixing frame and is positioned to contact an inner circumferential surface of a target object prior to the bent portion reaching a predetermined penetration depth, thereby mechanically limiting penetration depth of the bent portion by providing a physical stop that prevents the bent portion from being embedded in the target object beyond the predetermined depth.

4. The embolic apparatus of claim 3, each of the other plurality of second frame portions includes a respective bent portion on a respective distal end thereof, wherein each respective distal end is opposite to a respective proximal end connected to the main body portion.

* * * * *